(12) United States Patent
Hirata et al.

(10) Patent No.: US 10,379,017 B2
(45) Date of Patent: Aug. 13, 2019

(54) ANALYSIS APPARATUS

(71) Applicant: HORIBA, Ltd., Kyoto-shi, Kyoto (JP)

(72) Inventors: Yasushi Hirata, Kyoto (JP); Takahito Inoue, Kyoto (JP); Takuji Kurozumi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/031,892

(22) PCT Filed: Oct. 29, 2014

(86) PCT No.: PCT/JP2014/078740
§ 371 (c)(1),
(2) Date: Apr. 25, 2016

(87) PCT Pub. No.: WO2015/064631
PCT Pub. Date: May 7, 2015

(65) Prior Publication Data
US 2016/0266018 A1 Sep. 15, 2016

(30) Foreign Application Priority Data
Oct. 29, 2013 (JP) .................................. 2013-224706

(51) Int. Cl.
G01N 1/34 (2006.01)
G01N 1/44 (2006.01)
(Continued)

(52) U.S. Cl.
CPC ................. *G01N 1/34* (2013.01); *G01N 1/44* (2013.01); *G01N 33/0016* (2013.01);
(Continued)

(58) Field of Classification Search
CPC ........... G01N 1/44; G01N 31/12; G01N 25/20
See application file for complete search history.

(56) References Cited

U.S. PATENT DOCUMENTS 4,234,541 A * 11/1980 Bredeweg .............. G01N 31/12
  134/166 C
5,110,554 A * 5/1992 Tanimoto ................ F27B 17/02
  422/78
(Continued)

FOREIGN PATENT DOCUMENTS

CN 102511003 A 6/2012
JP S58-162864 A 9/1983
(Continued)

OTHER PUBLICATIONS

International Search Report dated Feb. 10, 2015 for PCT/JP2014/078740 and English translation.
(Continued)

*Primary Examiner* — Matthew D Krcha
(74) *Attorney, Agent, or Firm* — Lucas & Mercanti, LLP

(57) ABSTRACT

In order to surely discharge dust produced in a sample containing part 10, the present invention is adapted to include: a dust introduction part 30 that has a through-hole 3a formed penetrating in a vertical direction and introduces dust produced in the sample containing part 10 into the through-hole 3a; a dust containing part 43 that contains the dust discharged through the through-hole 3a; and a dust discharge path 41a of which one end is connected to the dust introduction part 30 to communicatively connect to the through-hole 3a and the other end is connected to the dust containing part 43, in which the dust discharge path 41a is linearly formed along the vertical direction from the one end to the other end.

13 Claims, 5 Drawing Sheets

(51) Int. Cl.
  *G01N 33/00* (2006.01)
  *G01N 31/12* (2006.01)
  *G01N 1/22* (2006.01)
  *F27D 19/00* (2006.01)

(52) U.S. Cl.
  CPC ...... *F27D 2019/0012* (2013.01); *G01N 31/12* (2013.01); *G01N 2001/227* (2013.01)

(56) References Cited

U.S. PATENT DOCUMENTS

| | | |
|---|---|---|
| 6,270,727 B1 | 8/2001 | Mitchell et al. |
| 2012/0036673 A1* | 2/2012 | Ford .......................... F23J 3/02 15/304 |

FOREIGN PATENT DOCUMENTS

| | | |
|---|---|---|
| JP | S59-99256 A | 6/1984 |
| JP | H04-044696 B2 | 7/1992 |
| JP | H055679 A | 1/1993 |
| JP | H06-117978 A | 4/1994 |
| JP | 6-45886 Y2 | 11/1994 |
| JP | H07-038963 U | 7/1995 |
| JP | 2000266741 A | 9/2000 |
| JP | 2010008111 A | 1/2010 |
| JP | 2012047737 A | 3/2012 |

OTHER PUBLICATIONS

Notification of Reasons for Refusal dated Sep. 1, 2016 from the corresponding Japanese Application; Patent Application No. 2015-545263; Total of 2 pages.
Extended European Search Report dated Feb. 15, 2017 from corresponding European Application No./Patent No. 14858696.9-1553 / 3064938 PCT/JP2014078740; Applicant: Horiba, Ltd.; Total of 8 pages.
Office Action dated Feb. 20, 2017 from corresponding Chinese Patent Application No. 201480058824.2; Applicant: Horiba, Ltd.; English translation of Office Action; Total of 9 pages.
Office Action dated Aug. 29, 2018 from the corresponding European Application No. 14858696.9.

* cited by examiner

ANALYSIS APPARATUS

CROSS REFERENCE TO RELATED APPLICATION

This Application is a 371 of PCT/JP2014/078740 filed on Oct. 29, 2014, which, in turn, claimed the priority of Japanese Patent Application No. JP2013-224706 filed on Oct. 29, 2013, both applications are incorporated herein by reference.

TECHNICAL FIELD

The present invention relates to an analysis apparatus such as an elemental analysis apparatus adapted to analyze elements such as carbon (C) and sulfur (S) contained in a sample such as steel, nonferrous metal, or ceramic.

BACKGROUND ART

As this sort of elemental analysis apparatus, there is one adapted to place in a heating furnace a crucible containing a sample, apply high frequency AC voltage to a coil provided around the crucible to heat and burn the sample in the crucible by high frequency induction heating, and from gas produced thereby, analyze elements contained in the sample.

As disclosed in Patent literature 1, the above-described elemental analysis apparatus is configured to include a dust suction mechanism as well as sucking dust through a through-hole formed on the side circumferential surface of the heating furnace to discharge the dust because dust such as soot is produced by burning the sample and when the measurement gas is adsorbed by the dust, a measurement error occurs.

CITATION LIST

Patent Literature

[Patent Literature 1]
Japanese Unexamined Patent Publication JP-A2000-266741

SUMMARY OF INVENTION

Technical Problem

However, in the above-described configuration, since the dust is sucked through the through-hole formed on the side circumferential surface of the heating furnace, a difference in sucking force occurs between the vicinity of the through hole and the side opposite to the through hole, and as a result, there occurs a problem that, for example, dust depositing on the side opposite to the through hole cannot be fully sucked to allow part of the dust to remain, and when the gas is adsorbed by the remaining dust, a measurement error occurs.

Therefore, the present invention is made in order to solve the above-described problem, and a main object thereof is to surely discharge dust produced in a heating furnace to accurately perform analysis.

Solution to Problem

That is, an analysis apparatus according to the present invention is an analysis apparatus that heats a sample in a sample containing part and analyzes gas produced thereby, and includes: a dust introduction part that has a through-hole formed penetrating in a vertical direction and introduces dust produced in the sample containing part into the through-hole; a dust containing part that contains the dust discharged through the through-hole; and a dust discharge path of which one end is connected to the dust introduction part to communicatively connect to the through-hole and the other end is connected to the dust containing part, in which the dust discharge path is linearly formed along the vertical direction from the one end to the other end.

In such a configuration, since the through-hole is formed penetrating in the vertical direction, the dust is discharged vertically downward through the through-hole, and therefore as long as the through-hole is formed in the central part of the sample containing part as viewed from vertically above, the dust can be surely discharged.

Further, since the dust discharge path is linearly formed along the vertical direction from the one end to the other end, the dust discharged through the through-hole can be discharged without remaining in the dust discharge path.

This makes it possible to surely discharge the dust produced in the sample containing part to make a measurement error due to the attachment of the gas to dust unlikely to occur, and thereby the analysis can be accurately performed.

Preferably, the analysis apparatus includes an up/down movement mechanism adapted to integrally move up or down the dust introduction part, the dust discharge path, and the dust containing part.

This makes it possible to move up or down the dust discharge path without deforming the dust discharge path, and therefore the bending of the dust discharge path can be prevented to make dust clogging and/or the deterioration of the dust discharge path unlikely to occur.

Preferably, the analysis apparatus includes: a supporting part that supports the dust introduction part; and a driving part that has a shaft member connected to the supporting part and moves up or down the supporting part, and the shaft member is arranged separately from the dust introduction part in a horizontal direction by a predetermined distance.

This makes it possible to provide the dust containing part below the dust introduction part to make the whole of the apparatus compact. In addition, by providing the dust containing part below the dust introduction part, it becomes easy to linearly form the dust discharge path along the vertical direction.

Preferably, the through-hole is formed in a rotating body shape.

This makes dust unlikely to clog the through-hole, and therefore the dust can be surely discharged to the dust discharge path through the through-hole.

Preferably, the analysis apparatus further includes an open/close mechanism that is provided in the dust discharge path and switches an open/close state of the dust discharge path. In this configuration, since the open/close mechanism is provided in the dust discharge path linearly formed along the vertical direction, when the open/close mechanism switches the dust discharge path to the close state, dust can be prevented from being sandwiched, and thereby the open/close state of the dust discharge path can be surely switched.

Consider here the case where the dust introduction part is attached to the sample containing part.

In this case, a configuration adapted to move up the above-described supporting part using, for example, a cylinder or the like, and thereby bring the dust introduction part close to the sample containing part for the attachment can be cited.

However, in this configuration, when the dust introduction part comes close to the sample containing part, the cylinder extends in its axial direction, and when attempting to align the axes of the dust introduction part and the sample containing part in this state, the cylinder makes a swinging motion to make it difficult to accurately align the axes. In addition, as described above, in the case where the cylinder is arranged separately from the dust introduction part by the predetermined distance, when aligning the axes, the cylinder makes a swinging motion at a position eccentric to the dust introduction part and the sample containing part, further increasing difficulty.

This causes a risk of attaching the dust introduction part to the sample containing part in a state where the axes are not accurately aligned, and if so, the airtightness between them cannot be ensured, causing possible air leakage.

As result, when the gas produced from the sample leaks, the problem of reduced measurement accuracy occurs.

Also, when providing, for example, a leak check mechanism in order to sense the gas leakage, the problem of increased size and cost of the whole of the apparatus occurs.

Further, as described above, if the cylinder makes a swing motion when aligning the axes of the dust introduction part and the sample containing part, the swing propagates to, for example, an actuator and the like constituting the cylinder to place a load on the actuator and the like, thus reducing the life of the apparatus.

Therefore, in order to attach the dust introduction part to the sample containing part in an airtight manner, preferably, the driving part further has a driving part main body into or out of which the shaft member moves; the shaft member moves into the driving part main body, and thereby the dust introduction part moves in a direction to block a downward opening formed in the sample containing part; and the shaft member moves out of the driving part main body, and thereby the dust introduction part moves in a direction to open the opening.

In this configuration, since the shaft member moves into the driving part main body, and thereby the dust introduction part moves in the direction to block the downward opening formed in the sample containing part to bring the dust introduction part and the sample containing part close to each other, when aligning the axes of them, the shaft member is stable with little swinging motion, and thereby the axes can be accurately aligned. This makes it possible to attach the dust introduction part to the sample containing part in an airtight manner, and therefore the gas leakage from between the dust introduction part and the sample containing part can be surely prevented from occurring.

In addition, as described above, since when aligning the axes of the dust introduction part and the sample containing part, the shaft member is stable with little swing motion, a load placed on the driving part main body when aligning the axes can be made as small as possible, and thereby a reduction in the life of the apparatus can be prevented.

Advantageous Effects of Invention

According to the present invention configured as described, the dust produced in the sample containing part can be surely discharged, and thereby a measurement error due to the attachment of the gas to dust can be made unlikely to occur, thus making it possible to accurately perform the analysis.

REFERENCE SIGNS LIST

Figure 1:
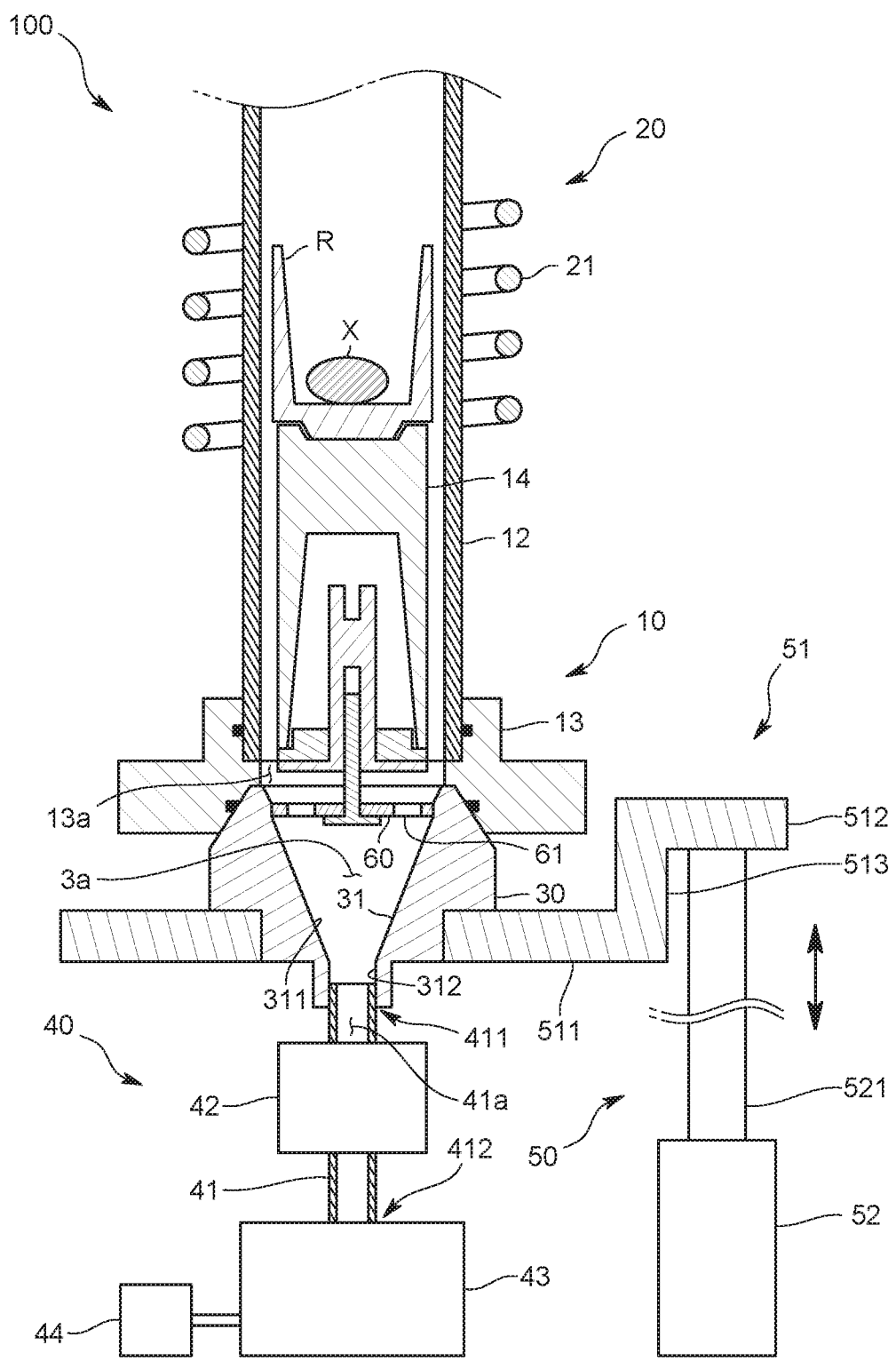
FIG. 1 is an overall view schematically illustrating the configuration of an analysis apparatus according to the present embodiment.

100 Elemental analysis apparatus
X Sample
10 Heating furnace
30 Dust introduction part
31 Introduction surface
3a Through-hole
40 Dust discharge mechanism
41a Dust discharge path
41 Dust discharge path forming member
42 Open/close mechanism
43 Dust containing part
50 Up/down movement mechanism Description Of Embodiments In the following, one embodiment of an elemental analysis apparatus 100 as an example of an analysis apparatus according to the present invention will be described with reference to drawings.

An elemental analysis apparatus 100 according to the present embodiment is one that for example, heats and burns a sample X such as metal, and from gas produced thereby, analyzes elements such as carbon (C) and sulfur (S) contained in the sample X.

Figure 2:
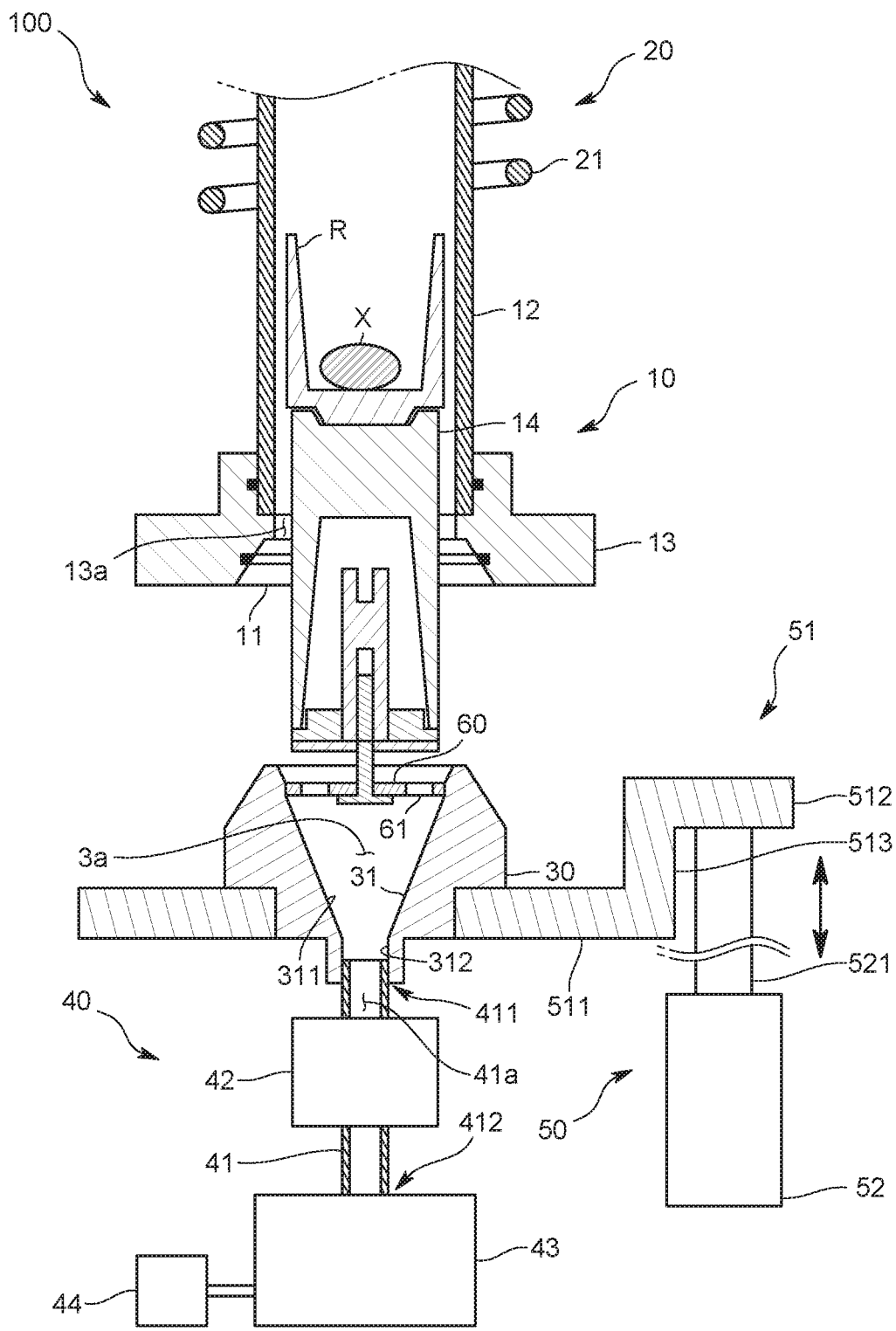
FIG. 2 is an overall view schematically illustrating the configuration of the analysis apparatus according to the same embodiment.

Specifically, as illustrated in FIGS. 1 and 2, the elemental analysis apparatus 100 is one including: a heating furnace 10 as a sample containing part in which a crucible R containing the sample X is placed; a heating mechanism 20 adapted to heat the sample X; an unillustrated gas analyzer adapted to analyze the gas produced by heating and burning the sample X; a dust introduction part 30 into which dust produced by burning the sample X is introduced; and a dust discharge mechanism 40 adapted to discharge the dust from inside the heating furnace 10.

In the following, the respective parts will be described.

The heating furnace 10 is configured to burn the sample X inside, and lead the gas produced thereby to the unillustrated gas analyzer, and as illustrated in FIGS. 1 and 2, is formed in a substantially tubular shape as well as having an opening 11 formed vertically downward.

Specifically, the heating furnace 10 includes: a furnace main body 12 formed in a substantially circular tube shape; and a block body 13 that is provided below the furnace main body 12 and has a communicative connection hole 13a communicatively connected to the inside of the furnace main body 12 and formed penetrating in the vertical direction.

More specifically, in the present embodiment, the opening 11 of the heating furnace 10 is one that is formed as a downward opening of the communicative connection hole 13a in a circular shape, and formed such that the central axis of the opening 11 and the tube axis of the furnace main body 12 coincide with each other.

Inside the above-described heating furnace 10, the crucible R is contained on a placement table 14.

The placement table 14 is provided vertically movable along the tube axial direction of the furnace main body 12 inside the furnace main body 12, and in the present embodiment, configured to be moved up or down by the below-described up/down movement mechanism 50 between a heating position where the sample X in the crucible R is heated inside the heating furnace 10 and an attachment/detachment position where the crucible R is positioned outside the heating furnace 10 and attached on or detached from the placement table 14.

The crucible R is one that contains the sample X inside and is attached on the placement table 14, and in the present embodiment, made of a magnetic material such as ceramic having an electrically conductive heating element.

The heating mechanism 20 is an induction current generating mechanism adapted to generate induction current in the sample X contained in the crucible R by high frequency induction heating, and specifically one including a coil 21 and an unillustrated power supply adapted to apply high frequency AC voltage to the coil 21. In the present embodiment, the coil 21 is provided along the outer circumference of the furnace main body 12, and the height of the placement table 14 is set such that when the high frequency AC voltage is applied to the coil 21, the crucible R is positioned inside the coil 21. When the high frequency AC voltage is applied to the coil 21, the electrically conductive heating element included in the crucible R generates heat by the high frequency induction heating to heat the sample X in the crucible R.

The unillustrated gas analyzer is one that analyzes the gas led to the gas analyzer and obtains the contents of respective components contained in the sample X, and in the present embodiment, one that performs the analysis using, for example, a non-dispersive infrared absorption method (NDIR method). Specifically, the gas analyzer has an unillustrated non-dispersive infrared detector, and is one that detects $CO_2$, $CO$, $SO_2$, and the like contained in the gas to thereby obtain the contents of carbon (C), sulfur (S), and the like contained in the sample X.

The dust introduction part 30 is one that has a through-hole 3a formed penetrating in the vertical direction, and is also one that is provided so as to close the vertically downward opening 11 formed in the heating furnace 10 in a state where the placement table 14 is in the heating position, and introduces the dust produced by burning the sample X into the through-hole 3a. More specifically, the dust introduction part 30 in the present embodiment is arranged with the upper part of the dust introduction part 30 being fitted into the communicative connection hole 13a formed in the block body 13 via, for example, a seal member.

Specifically, as illustrated in FIGS. 1 and 2, the dust introduction part 30 is formed in a block body shape, and in the center thereof, the through-hole 3a that penetrates through the dust introduction part 30 in the vertical direction and communicatively connects to the inside of the heating furnace 10 is formed, and also an introduction surface 31 adapted to introduce the dust into the through-hole 3a to discharge it is formed.

The through-hole 3a is formed in a rotating body shape, and also formed such that the rotational axis thereof coincide with the tube axis of the heating furnace 10, i.e., with the central axis of the opening 11. More specifically, the through-hole 3a is a space surrounded by the inner circumferential surface of the dust introduction part 30, and in the present embodiment, formed as a space surrounded by: a first inner circumferential surface 311, which is formed in an inverted truncated conical shape of which the diameter decreases vertically downward; and a second inner circumferential surface 312, which is formed continuously with the first inner circumferential surface 311, linearly extends vertically downward, and has a uniform circular-shaped cross section.

The introduction surface 31 is symmetrically formed with the through-hole 3a as the center, and in the present embodiment, a tilted surface formed in a rotating body shape with the tube axis of the heating furnace 10 as the central axis, of which at least part is formed of the first inner circumferential surface 311. Specifically, the introduction surface 31 is formed in an annular shape as viewed from vertically above.

The above-described configuration and activation of the below-described dust discharge mechanism 40 make it possible to create a substantially uniform flow from the heating furnace 10 toward the through-hole 3a, and discharge the dust through the through-hole 3a. That is, the dust flow toward the through-hole 3a from a dust production part (crucible R and the like) where the dust is produced is rotationally symmetric on a cross section along the vertical direction.

The dust introduction part 30 is fixed with the above-described placement table 14, and the present embodiment is configured such that the dust introduction part 30 and the placement table 14 are connected to each other via a connecting member 60 provided on the inner circumferential surface of the dust introduction part 30 and make the up/down movement integrally.

The connecting member 60 is one that is formed in a flat plate shape, and formed with multiple holes 61 penetrating in the thickness direction. The multiple holes 61 are symmetrically positioned with reference to the center of the connecting member 60 as well as being formed along the circumferential direction so as to make the distance between any adjacent two of the holes 61 constant, and it is configured that the dust produced in the heating furnace 10 passes through the holes 61 and are introduced into the through-hole 3a.

The dust introduction part 30 configured as described above is provided with the up/down movement mechanism 50 adapted to move up or down the dust introduction part 30 along the vertical direction.

The up/down movement mechanism 50 is one including: a supporting part 51 that supports the dust introduction part 30; and a driving part 52 that has a shaft member 521 connected to the supporting part 51 and moves up or down the supporting part 51 along the vertical direction.

The supporting part 51 is one configured to be able to arrange the shaft member 521 separately from the dust introduction part 30 in the horizontal direction, and has: a first plate member 511 that extends in the horizontal direction and is formed in a flat plate shape; a connecting plate 513 that is connected to the first plate member 511 at the lower end thereof and upright from the first plate member 511; and a second plate member 512 that extends from the upper end of the connecting plate 513 in the horizontal direction toward the side opposite to the first plate member 511. Note that in the present embodiment, the first plate member 511, the second plate member 512, and the connecting member 513 are integrally formed.

The first plate member 511 is one adapted to support the dust introduction part 30, and fixed with the dust introduction part 30 by, for example, unillustrated screws or the like.

The second plate member 512 is positioned on the vertically upper side separately from the first plate member 511 by a predetermined distance, and supported by the shaft member 521.

The driving part 52 is one that moves up or down the supporting part 51 along the vertical direction at a position offset from the dust introduction part 30 in the horizontal direction. Specifically, the driving part 52 is configured to move up or down the shaft member 521 supporting the second plate member 512, and in the present embodiment, uses a cylinder.

The shaft member 521 is arranged separately from the dust introduction part 30 in the horizontal direction keeping a distance preventing overlap with at least dust introduction part 30 as viewed from vertically below. In the present embodiment, the central axis of the shaft member 521 is arranged separately in the horizontal direction from each of the central axis of the dust introduction part 30, the rotational axis of the through-hole 3a, and the tube axis of the heating furnace 10. That is, the shaft member 521 is arranged at a position preventing overlap with the opening 11 of the heating furnace 10, the dust introduction part 30, and the below-described dust discharge path 41a as viewed from vertically below, and this makes it possible to arrange the below-described dust containing part 43 vertically below the opening 11 and the dust introduction part 30.

The shaft member 521 of the driving part 52 moves up or down the supporting part 51 along the vertical direction, and thereby the up/down mechanism 50 configured as described can move up or down the dust introduction part 30 supported by the supporting part 51 along the vertical direction.

Note that as described above, the dust introduction part 30 is connected to the placement table 14 via the connecting member 60, and therefore the placement table 14 moves up or down together with the dust introduction part 30.

That is, the up/down movement mechanism 50 is configured to move up or down the dust introduction part 30 as the shaft member 521 moves up or down, and also move up or down the crucible R placed on the placement table 14 between the heating position and the attachment/detachment position.

Subsequently, the dust discharge mechanism 40 will be described.

The dust discharge mechanism 40 is one that discharges the dust produced in the heating furnace 10 from the heating furnace 10, and includes: a dust discharge path forming member 41 that forms the dust discharge path 41a communicatively connecting to the through-hole 3a; an open/clos mechanism 42 that is provided in the dust discharge path forming member 41 to switch an open/close state of the dust discharge path 41a; the dust containing part 43 that is provided on the downstream side of the dust discharge path 41a to contain the dust discharged through the dust discharge path 41a; and a suction mechanism 44 that is connected to the dust containing part 43 to suck air inside the dust containing part 43.

The dust discharge path forming member 41 is one adapted to discharge the dust vertically downward, and as illustrated in FIG. 1, also one that forms the dust discharge path 41a inside which the dust flows and is formed in a straight tube shape. More specifically, the dust discharge path forming member 41 is one that is formed of resin or the like and has elasticity, and in the present embodiment, a silicon tube such as a Fluran tube.

The dust discharge path forming member 41 is configured such that the outside diameter thereof is equal to the opening size of the second inner circumferential surface 312 of the dust introduction part 30, and one end part 411 of the dust discharge forming member 41 is fitted to the second inner circumferential surface 312 without backlash to communicatively connect the dust discharge path 41a and the through-hole 3a to each other. Also, the other end part 412 of the dust discharge path forming member 41 is connected to the below-described dust containing part 43. Note that the dust discharge forming member 41 in the present embodiment is configured to move up or down integrally with the dust introduction part 30 along with the up/down movement of the dust introduction part 30 in a state where the one end part 411 is fitted to the second inner circumferential surface 312.

The dust discharge path 41a is one of which one end is connected to the dust introduction part 30 to communicatively connect to the through-hole 3a and also the other end is connected to the dust containing part 43 to lead the dust to the dust containing part 43 through the through-hole 3a, and in the present embodiment, linearly formed along the vertical direction from the one end to the other end.

The above-described dust discharge path forming member 41 is provided with the open/close mechanism 42 adapted to switch the dust discharge path 41a to the open state or the close state. Note that the open/close mechanism 42 in the present embodiment is one that is controlled by an unillustrated control part so as to, when performing the analysis, switch the dust discharge path 41a to the close state, and when discharging the dust, switch the dust discharge path 41a to the open state.

In the present embodiment, the open/close mechanism 42 uses a pinch valve, and is configured to switch the dust discharge path 41a from the open state to the close state by crushing the silicon tube as the dust discharge path forming member 41. In addition, while the open/close mechanism 42 switches the dust discharge path 41a to the close state, dust deposits at a position where the dust discharge path 41a is crushed.

The dust containing part 43 is provided on the downstream side of the dust discharge path 41a, and in the present embodiment, for example, a substantially rectangular parallelepiped shaped dust box arranged vertically below the through-hole 3a of the dust introduction part 30.

More specifically, the dust containing part 43 is configured to be attachable to or detachable from the other end part 412 of the dust discharge path forming member 41, and in a state of being attached to the other end part 412 of the dust discharge path forming member 41, move up or down integrally with the dust discharge path forming member 41 and the dust introduction part 30.

Note that in the present embodiment, an unillustrated supporting mechanism adapted to support the dust containing part 43 as well as integrally moving up or down the dust containing part 43 and the dust introduction part 40 is connected to the supporting part 51. This configuration allows the dust containing part 43 connecting with the dust introduction part 30 and the dust discharge path forming member 41 to integrally move up or down as well.

That is, the present embodiment is configured such that the dust introduction part 30, dust discharge path forming member 41, open/close mechanism 42, and dust containing part 43 move up or down while keeping the relative positional relationship among them.

The above-described dust containing part 43 is provided with the suction mechanism 44 adapted to suck air inside the dust containing part 43, and the suction mechanism 44 is configured to, when discharging the dust, after the open/close mechanism 42 switches the dust discharge path 41a to the open state, suck air from inside the dust containing part 43 to decrease the inner pressure of the heating furnace 10. In addition, by activating the suction mechanism 44, the dust produced in the heating furnace 10 is discharged vertically downward through the through-hole 3a, passes through the dust discharge path 41a vertically downward, and is led to the dust containing part 43.

Note that the suction mechanism 44 may be one that moves up or down integrally with the dust containing part 43, or one that is placed at a fixed position without moving up or down integrally with the dust containing part 43.

The elemental analysis apparatus 100 according to the present embodiment configured as described can surely discharge the dust produced in the heating furnace 10 because the dust introduction part 30 is formed in the rotating body shape with the tube axis of the heating furnace 10 as the rotational axis, and the dust is discharged vertically downward through the through-hole 3a formed in the central part of the dust introduction part 30. This makes it possible to make a measurement error due to the attachment of the gas to dust unlikely to occur, and thereby the analysis can be accurately performed.

Also, since the introduction surface 31 is formed in an annular shape as viewed from vertically above, and a tilted surface formed in a rotating body shape with the tube axis of the heating furnace 10 as the central axis, the dust can be surely discharge without remaining on the introduction surface 31.

Further, since the second inner circumferential surface 312 and the dust discharge path 41a are linearly formed along the vertical direction, clogging with dust due to the bend or the like of the through-hole 3a or the dust discharge path 41a can be prevented at the time of discharging the dust, and therefore the dust can be more surely discharged. This makes it possible to prevent dust from being sandwiched when the open/close mechanism 42 crushes the dust discharge forming member 41 to switch it to the close state.

In addition, since the dust introduction part 30, dust discharge path forming member 41, and dust containing part 43 are configured to integrally move up or down, each of the members does not expand or contract along with the up/down movement, and therefore each of the members can be prevented from being deteriorated due to the up/down movement. Further, clogging with dust due to the bend of the dust discharge path 41a can also be prevented.

Also, since the central axis of the shaft member 521 is arranged offset in the horizontal direction from the central axis of the dust introduction part 30, the rotational axis of the through-hole 3a, and the tube axis of the heating furnace 10, the dust containing part 43 can be provided below the dust introduction part 30, making it easier to linearly form the dust discharge path 41a along the vertical direction, and in addition, the element analysis apparatus 100 can be made compact.

Further, since the supporting part 51 has the first plate member 511 and the second plate member 512 arranged offset from the first plate member 511, the distance the shaft member 521 of the driving part 52 moves up or down can be set to be long without increasing the height dimension of the entire apparatus.

Note that the present invention is not limited to the above-described embodiment.

For example, the above-described embodiment is configured to discharge the dust using the suction mechanism, but may be configured to transfer the dust under pressure vertically downward to discharge it by pressurizing the inside of the heating furnace.

Also, in the above-described embodiment, the dust introduction part has the one through-hole, but may be configured to have multiple through-holes. In this case, preferably, the multiple through-holes are arranged symmetrically with respect to the tube axis of the heating furnace.

Further, it may be configured to form an air circulation path in the block body, and sent air into the communicative connection hole of the block body through the air circulation path. By configuring as described above, air can be blown to dust depositing on the connecting member to drop it through the holes formed in the connecting member. This makes it possible to more surely introduce the dust produced in the heating furnace into the dust introduction part.

Further, it may be adapted to directly suck and discharge the dust depositing on the connecting member through the air circulation path.

Still further, in the above-described embodiment, the dust discharge path forming member is formed in a straight tube shape, but may be formed in a bellows shape.

In addition, in the above-described embodiment, the pinch valve is used for the open/close mechanism, but it may be configured to use an on/off valve, solenoid valve, or the like to switch the dust discharge path between the open state and the close state.

Also, the above-described embodiment is adapted such that when discharging the dust, the open/close mechanism switches the dust discharge path to the open state, and then the suction mechanism is activated to discharge the dust, but may be adapted such that in a state where the suction mechanism is activated, the open/close mechanism switches the dust discharge path from the close state to the open state to discharge the dust.

Further, in the above-described embodiment, the coil is provided along the outer circumference of the furnace main body, but may be provided, for example, at the bottom part of the crucible, or on the upper surface of the placement table.

Figure 3:
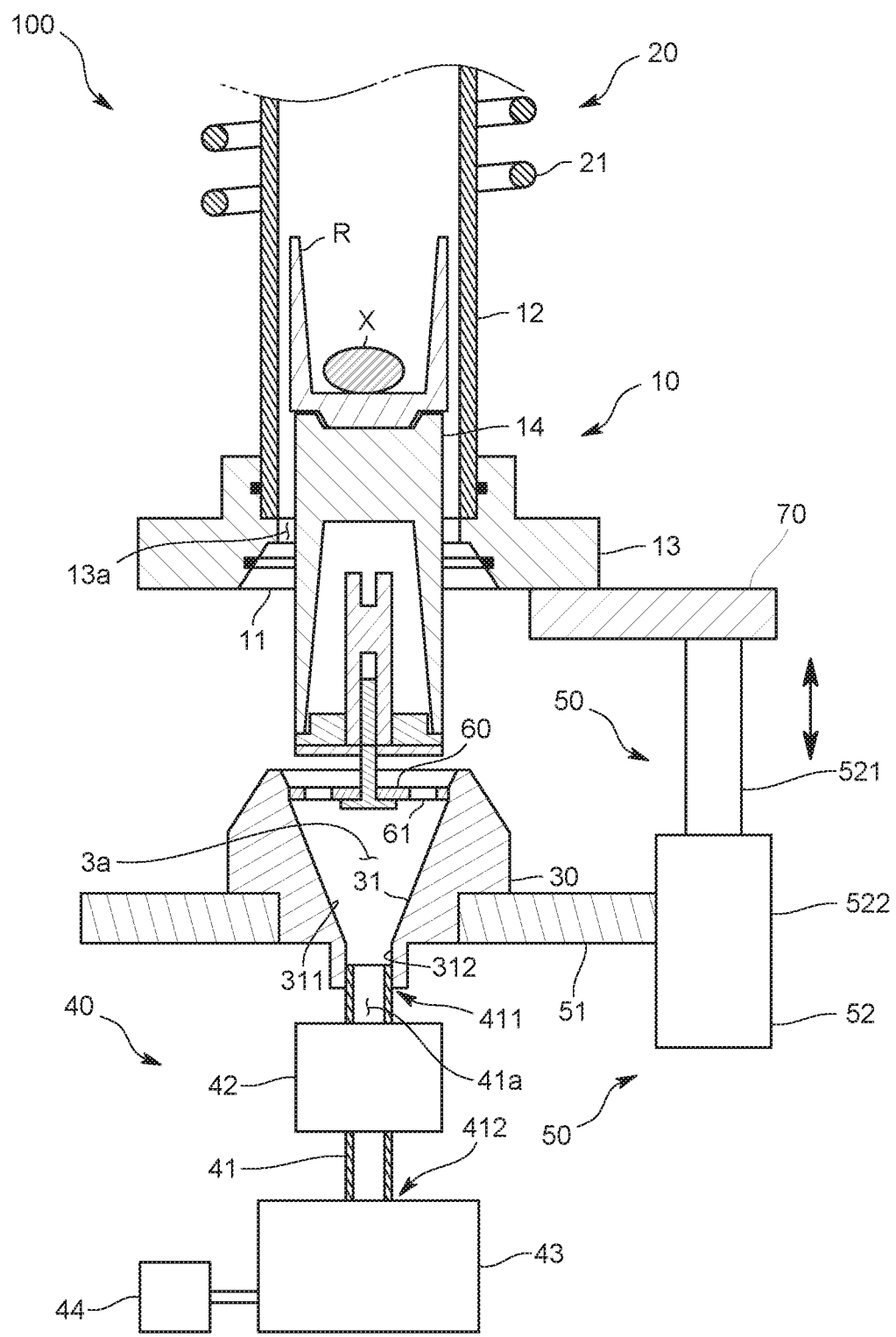
FIG. 3 is an overall view schematically illustrating the configuration of an analysis apparatus according to another embodiment.
Figure 4:
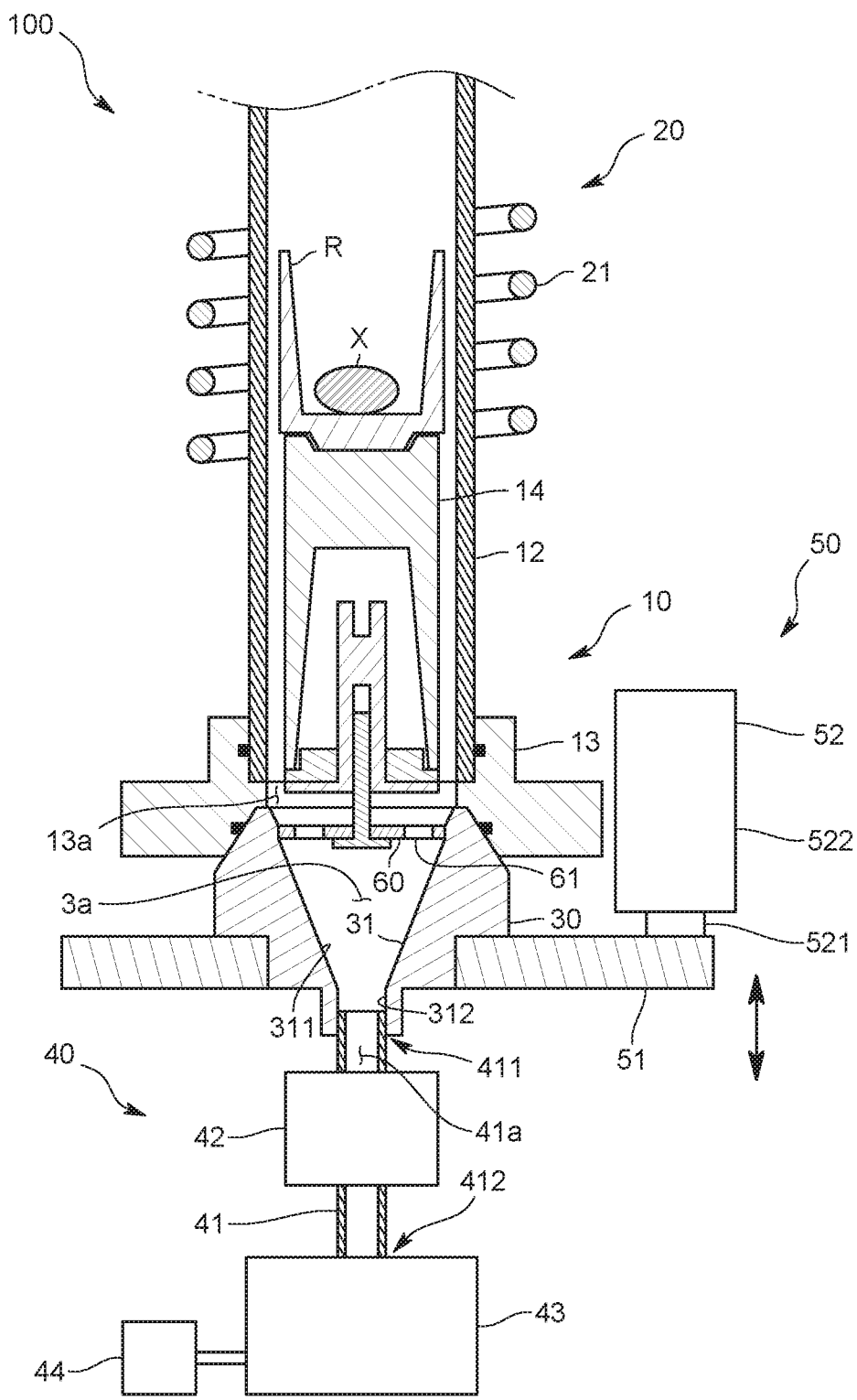
FIG. 4 is an overall view schematically illustrating the configuration of an analysis apparatus according to still another embodiment.
Figure 5:
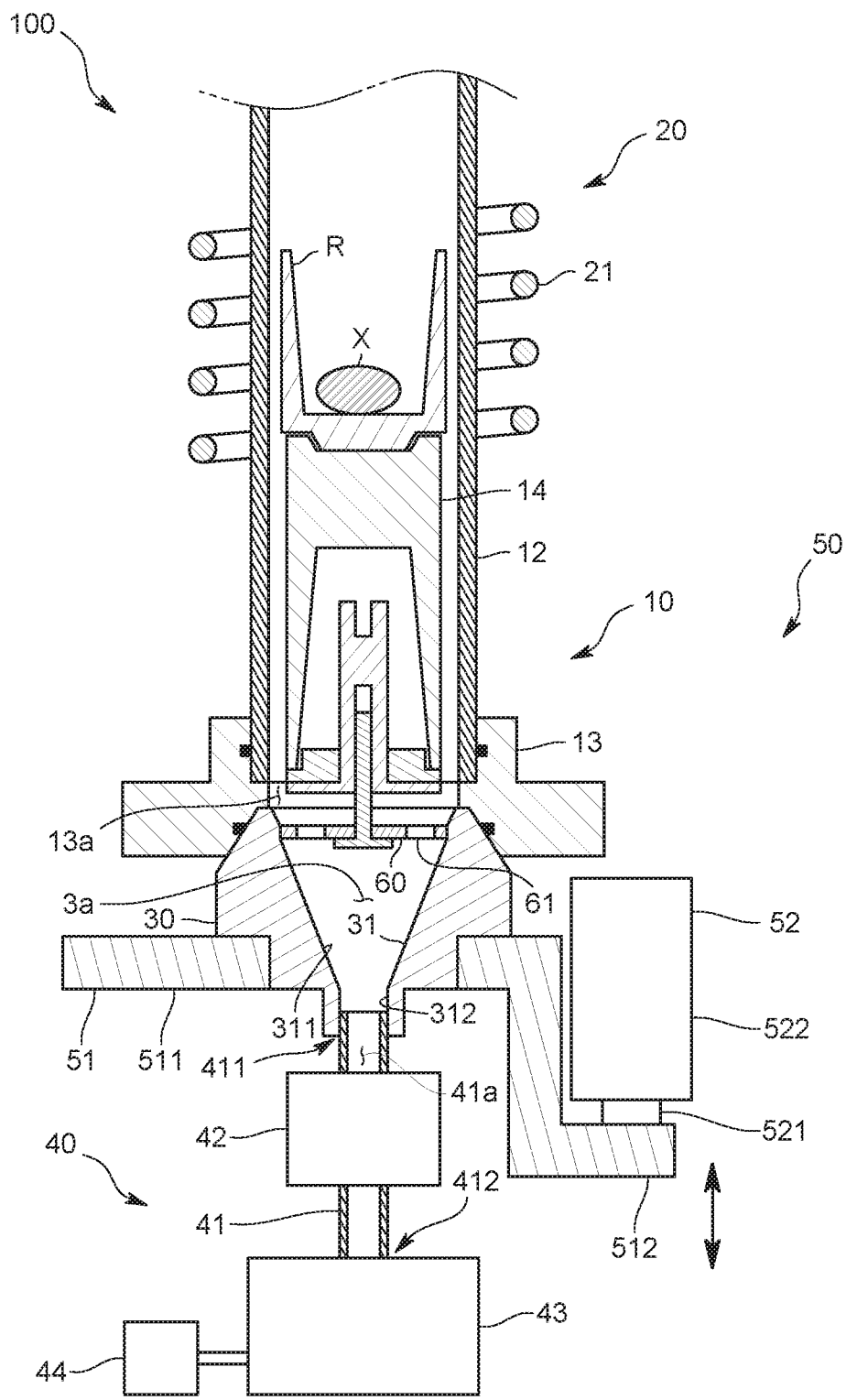
FIG. 5 is an overall view schematically illustrating the configuration of an analysis apparatus according to yet another embodiment.

Still further, the above-described embodiment is configured such that the shaft member is extended, and thereby the dust introduction part is brought close to and attached to the heating furnace, but may be configured such that, for example, as illustrated in FIGS. 3 to 5, the driving part 52 further has a driving part main body 522 into or out of which the shaft member 521 moves, and the shaft member 521 moves into the driving part main body 522, by which the dust introduction part 30 is brought close to and attached to the heating furnace 10, whereas the shaft member 521 moves out of the driving part main body 522, by which the dust introduction part 30 is separated from the heating furnace 10.

Specifically, the driving part is, for example, an air cylinder, and configured such that the length of a part of the shaft member 521 protruding from the driving part main body 522 increases or decreases along the axial direction.

More detailed configurations will be exemplified in FIGS. 3 to 5.

In the analysis apparatus 100 illustrated in FIG. 3, the shaft member 521 is fixed to the heating furnace 10, and also the driving part main body 522 is fixed with the supporting part 51 supporting the dust introduction part 30. In this analysis apparatus 100, the shaft member 521 is fixed to the block body 13 constituting the heating furnace 10 via an intermediate member 70 intervening between the heating furnace 10 and the shaft member 521, and the driving part main body 522 is directly fixed to the supporting part 51 in a position offset in the horizontal direction from the dust introduction part 30. Note that the shaft member 521 may be directly fixed to the block body 13, and the driving part main body 522 may be indirectly fixed to the supporting part 51.

In this configuration, when the shaft member 521 moves into the driving part main body 522, the dust introduction part 30 moves up to come close to the heating furnace 10 together with the driving part main body 522, and therefore when aligning the axes of the dust introduction part 30 and the heating furnace 10, the shaft member 521 is stable with little swinging motion, making it possible to accurately align the axes.

Also, around the heating furnace 10, for example, various components constituting the analysis apparatus 100 are arranged; however, the above-described configuration makes it possible to provide the driving part main body 522 below the heating furnace 10, and thereby a dead space below the heating furnace 10 can be effectively utilized.

Further, by providing the driving part main body 522 below the heating furnace 10, the driving part main body 522 and the shaft member 521 can be kept away from the coil 21 applied with the high frequency AC voltage, and therefore the heat effect and/or the like from the coil 21 on the driving part main body 522 and the shaft member 521 can be reduced.

In addition, the analysis apparatus 100 according to the above-described embodiment is configured such that the up/down movement mechanism 50 moves up or down the dust introduction part 30 in a state where the block body 13 and the driving part 52 are fixed to, for example, a shared frame body; however, the above-described analysis apparatus 100 illustrated in FIG. 3 does not require fixing the driving part 52 to a frame body adapted to fix the block body 13. This makes it possible to reduce the size of the frame body and also, for example, when aligning the axes of the dust introduction part 30 and the heating furnace 10, makes it easier to adjust the position of the driving part 52.

Also, the analysis apparatus 100 illustrated in FIG. 4 is configured such that the shaft member 521 is fixed with the supporting part 51 supporting the dust introduction part 30, and the shaft member 521 contracts toward the driving part main body 522 provided above the supporting part 51. In this analysis apparatus 100, the shaft member 521 is directly fixed to the supporting part 51, and the driving part main body 522 is indirectly fixed to the block body 13 constituting the heating furnace 10 via an unillustrated intermediate member intervening between the heating furnace 10 and the driving part main body 522. Note that the shaft member 521 may be indirectly fixed to the supporting part 51, and the driving part main body 522 may be directly fixed to the block body 13.

In this configuration, when the shaft member 521 moves into the driving part main body 522, the dust introduction part 30 moves up to come close to the heating furnace 10, and therefore when aligning the axes of the dust introduction part 30 and the heating furnace 10, the shaft member 521 is stable with little swinging motion, making it possible to accurately align the axes.

Further, in the analysis apparatus 100 illustrated in FIG. 5, the supporting part 51 is formed in a shape bending downward, and has the first plate member 511 adapted to support the dust containing part and a second plate member 512 positioned below the first plate member 511, and the second plate member 512 is fixed with the shaft member 521. In this analysis apparatus 100, the shaft member 521 is directly fixed to the second plate member 512, and the driving part main body 522 is indirectly fixed to the block body 13 constituting the heating furnace 10 via an unillustrated intermediate member intervening between the heating furnace 10 and the driving part main body 522. Note that the shaft member 521 may be indirectly fixed to the second plate member 512, and the driving part main body 522 may be directly fixed to the block body 13.

In this configuration, when the shaft member 521 moves into the driving part main body 522, the dust introduction part 30 moves up to come close to the heating furnace 10, and therefore when aligning the axes of the dust introduction part 30 and the heating furnace 10, the shaft member 521 is stable with little swinging motion, making it possible to accurately align the axes.

Also, since the shaft member 521 is fixed to the second plate member 512 positioned below the first plate member 511, as compared with the analysis apparatus 100 illustrated in FIG. 4, the whole of the apparatus can be downsized in the height direction. Further, the driving part main body 522 and the shaft member 521 can be kept away from the coil 21 applied with the high frequency AC voltage, and therefore the heat effect and/or the like from the coil 21 on the driving part main body 522 and the shaft member 521 can be reduced.

In addition, in the analysis apparatus 100 illustrated in FIG. 5, the second plate member 512 is fixed with the shaft member 521; however, the second plate member 512 may be fixed with the driving part main body 522, and the shaft member 521 may be fixed to the block body 13 constituting the heating furnace 10 via an intermediate member intervening between the heating furnace 10 and the shaft member 521.

This makes it possible to obtain the same working effect as that of the analysis apparatus 100 illustrated in FIG. 5, and in addition, the driving part 52 is not required to be fixed to a frame body adapted to fix the block body 13, thus making it possible to reduce the size of the frame body, as well as for example, when aligning the axes of the dust introduction part 30 and the heating furnace 10, making it easier to adjust the position of the driving part 52.

Note that the present invention may be an analysis apparatus that heats a sample in a sample containing part and analyze gas produced thereby, and includes: a dust introduction part that has a through hole formed penetrating in a vertical direction, and introduces dust produced in the sample containing part into the through-hole; a supporting part adapted to support the dust introduction part; and a driving part adapted to move up or down the supporting part, in which the driving part is connected to the supporting part, and has a shaft member arranged separately from the dust introduction part in a horizontal direction by a predetermined distance, and a driving part main body into or out of which the shaft member moves, and the shaft member moves into the driving part main body, by which the dust introduction part moves in a direction to block a downward opening formed in the sample containing part, whereas the shaft member moves out of the driving part main body, by which the dust introduction part moves in a direction to open the opening.

Besides, it goes without saying that the present invention is not limited to any of the above-described embodiments, but can be variously modified without departing from the scope thereof.

INDUSTRIAL APPLICABILITY

According to the present invention, the dust produced in the sample containing part can be surely discharged, and thereby a measurement error due to the attachment of the gas to dust can be made unlikely to occur, thus making it possible to accurately perform the analysis.

The invention claimed is:

1. An analysis apparatus that heats a sample in a sample containing part and analyzes gas produced thereby, the analysis apparatus comprising:
a dust introduction part that has a through-hole formed penetrating in a vertical direction and introduces dust produced in the sample containing part into the through-hole;
a dust containing part that contains the dust discharged through the through-hole; and
a dust discharge path forming member forming a linear dust discharge path with a first end opening and a second end opening, the first end opening is connected to the dust introduction part to communicatively connect to the through-hole and the second end opening is connected to the dust containing part,
wherein the dust discharge path is linearly formed along the vertical direction from the first end opening to the second end opening, a center axis of the sample containing part passes through both the first end opening and the second end opening, and the dust introduction part, the dust containing part, and the dust discharge path are arranged linearly along the vertical direction.

2. The analysis apparatus according to claim 1, comprising
an up/down movement mechanism adapted to integrally move up or down the dust introduction part, the dust discharge path, and the dust containing part.

3. The analysis apparatus according to claim 1, wherein the through-hole is formed symmetrically about a rotational axis.

4. The analysis apparatus according to claim 1, further comprising
an open/close mechanism that is provided in the dust discharge path and switches an open/close state of the dust discharge path.

5. The analysis apparatus according to claim 1, further comprising a connecting member connecting the dust introduction part to a placement table holding the sample, the connecting member being a flat plate with through holes connected at an inner circumferential surface of the dust introduction part.

6. The analysis apparatus according to claim 1, wherein an entire length of the dust discharge path between the dust introduction part and the dust containing part is linear and vertical.

7. The analysis apparatus according to claim 1, further comprising:
a supporting part that supports the dust introduction part, and
a driving part that has a shaft member connected to the supporting part and moves up or down the supporting part,
wherein the shaft member is offset from a central axis of the dust introduction part in a horizontal direction.

8. The analysis apparatus according to claim 1, wherein the dust introduction part sealingly closes a downward opening in the sample containing part and introduces dust produced by burning the sample into the through-hole.

9. An analysis apparatus that heats a sample in a sample containing part and analyzes gas produced thereby, the analysis apparatus comprising:
a dust introduction part that has a through-hole formed penetrating in a vertical direction and introduces dust produced in the sample containing part into the through-hole,
a dust discharge path forming part that forms a linear dust discharge path along a vertical axis, the dust introduction part and the dust discharge path being configured to create a substantially uniform flow from the sample containing part toward the through-hole to discharge the dust through the through-hole,
the dust discharge path having a first end opening connected to the dust introduction part and a second end opening, a center axis of the sample containing part passes through both the first end opening and the second end opening, and the dust introduction part, the dust containing part, and the dust discharge path are arranged linearly along the vertical direction.

10. The analysis apparatus according to claim 7, wherein:
the driving part further has a driving part main body into or out of which the shaft member moves;
the shaft member moves into the driving part main body, and thereby the dust introduction part moves in a direction to block a downward opening formed in the sample containing part; and
the shaft member moves out of the driving part main body, and thereby the dust introduction part moves in a direction to open the opening.

11. The analysis apparatus according to claim 9, further comprising a connecting member connecting the dust introduction part to a placement table holding the sample, the connecting member being a flat plate with through holes connected at an inner circumferential surface of the dust introduction part.

12. The analysis apparatus according to claim 9, wherein an entire length of the dust discharge path between the first end opening and the second end opening is linear and vertical.

13. The analysis apparatus according to claim 9, further comprising:
a supporting part that supports the dust introduction part, and
a driving part that has a shaft member connected to the supporting part and moves up or down the supporting part,
wherein the shaft member is offset from a central axis of the dust introduction part in a horizontal direction.

* * * * *